United States Patent [19]
Nelson

[11] Patent Number: 4,708,886
[45] Date of Patent: Nov. 24, 1987

[54] ANALYSIS SYSTEM

[75] Inventor: Larry A. Nelson, Spokane, Wash.

[73] Assignee: Fisher Scientific Company, Pittsburgh, Pa.

[21] Appl. No.: 706,072

[22] Filed: Feb. 27, 1985

[51] Int. Cl.$^4$ ............... G01N 35/04; G01N 21/07
[52] U.S. Cl. ............... 422/72; 165/26; 422/63; 422/64; 422/67
[58] Field of Search ............... 422/63-67, 422/100, 72; 62/526; 165/26

[56] References Cited

U.S. PATENT DOCUMENTS

| | | | |
|---|---|---|---|
| 3,617,222 | 11/1971 | Matte | 422/64 |
| 3,856,470 | 12/1974 | Cullis et al. | 422/72 |
| 4,113,436 | 4/1978 | Werder et al. | 422/67 |
| 4,118,280 | 10/1978 | Charles et al. | 356/244 |
| 4,200,607 | 4/1980 | Suzuki . | |
| 4,260,581 | 4/1981 | Sakurada | 422/65 |
| 4,338,279 | 7/1982 | Orimo et al. | 422/64 |
| 4,363,781 | 12/1982 | Akamatsu et al. | 422/67 |
| 4,483,823 | 11/1984 | Umetsu et al. | 422/67 |
| 4,580,897 | 4/1986 | Nelson et al. | 422/64 |

FOREIGN PATENT DOCUMENTS 74102  3/1983 European Pat. Off. .
122772 10/1984 European Pat. Off. .

Primary Examiner—Michael S. Marcus

[57] ABSTRACT

An analysis system has a first storage area in which sample and reagent materials are stored at an appropriate storage temperature and a second (analysis) area which is maintained at a controlled and stabilized higher temperature at which the analysis is to be performed. A plurality of analysis cuvettes of long thermal time constant material are stored adjacent the second storage area for time intervals sufficient for those analysis cuvettes to be equilibrated to the analysis temperature. A transport mechanism in the second storage area is adapted to transport the equilibrated analytical cuvettes sequentially from the supply station to a load station, then to an analysis station and then to a used cuvette station, and a transfer mechanism is arranged for movement between the first and second storage areas for transferring quantities of sample and reagent from the first storage for loading into the equilibrated analytical cuvette at the loading station in the second storage area.

18 Claims, 6 Drawing Figures

ANALYSIS SYSTEM

This invention relates to liquid handling to systems, and apparatus for the analysis of fluid samples, and has particular application to apparatus for the analysis of constituents of biological fluids such as blood.

Many chemical analyses must be conducted at controlled and stable temperatures as the involved chemical reactions are temperature sensitive. In conventional clinical analysis systems, for example, raw or dilute sample is mixed with one or more reactants for analysis, and the resulting mixture is maintained in an incubator region to stabilize the temperature of the mixture at the desired analysis temperature, for example, 37° C., a temperature substantially higher than the temperature at which sample and reagent materials are stored.

Clinical analyzers are useful in performing a variety of analyses, including kinetic and endpoint analyses, by techniques such as absorption, light scattering, and/or fluorescence. Such analyzer systems typically are of the serial type (continuous flow or discrete) or of the parallel type in which analyses of several samples are performed concurrently. Centrifugal analyzers are of the parallel type and conventionally use a multicuvette rotor (sometimes termed a transfer disc) which provides a circumferential array of spaced elongated radially extending plural chamber cuvettes, each of which has a first chamber for initially holding a first reactant (frequently a sample of blood or other biological fluid), and a second chamber for initially holding one or more different reactants. Conventionally, a pipette module is used to load the several cuvettes of a rotor a small quantity of sample (for example 2–20 microliters) typically being loaded into one chamber and reactants in larger quantities (for example up to about 200 microliters) being loaded into the other chamber. After loading, each rotor is conventionally incubated to equilibrate the rotor and the reactants in its several cuvettes to analysis temperature. After the loaded rotor has reached the desired analysis temperature, the rotor is placed in an analysis module where the reactants are transferred by centrifugal force to analysis regions at the outer end of the cuvettes for mixing and reaction and subsequent analysis by photometric or other appropriate analysis technique. In a typical analysis sequence, the rotor is first spun at 100 rpm, then accelerated to about 4000 rpm for about one second for transferring the reactants from the inner chamber, then braked for mixing the sample and reactants, and then brought up to an analysis speed (typically 500–1000 rpm) for analysis.

Such analyzers are commonly used for the analysis of biological fluids such as blood, blood plasma or serum components, and perform absorbance mode analyses for glucose, cholesterol, creatinine, total protein, calcium, phosphorous, enzymes, and the like; and fluorescence or light scattering mode analyses for glucose, bile acids, phenytoin, pheophylline, gentamycin and the like.

In accordance with one aspect of the invention, there is provided an analysis system which has a first storage area in which sample and reagent materials are stored at an appropriate storage temperature and a second (analysis) area which is maintained at a controlled and stabilized higher temperature at which the analysis is to be performed. A plurality of analysis cuvettes of long thermal time constant material are stored adjacent the second storage area for time intervals sufficient for those analysis cuvettes to be equilibrated to the analysis temperature. A transport mechanism in the second storage area is adapted to transport the equilibrated analytical cuvettes sequentially from the supply station to a load station, then to an analysis station and then to a used cuvette station, and a transfer mechanism is arranged for movement between the first and second storage areas for transferring quantities of sample and reagent from the first storage area for loading into the thermally equilibrated analytical cuvette at the loading station in the second storage area.

In accordance with another aspect, there is provided a thermally insulated compartment with a storage region for a plurality of analysis cuvettes of long thermal time constant material, a loading region, an analysis station with measuring apparatus in its sensing relation to an analysis cuvette at said analysis station, and transfer mechanism for transporting cuvettes sequentially from said storage station to said loading station for loading with sample and reactant materials and then to said analysis station for chemical analysis. A gas at a controlled stabilized analysis temperature is circulated through the storage region to provide efficient thermal interchange between the stored cuvettes to stabilize the temperature of those stored cuvettes at the analysis temperature prior to transfer from the storage area to the loading station for loading with sample and reactant materials.

In a particular embodiment, the system is of the centrifugal analyzer type and multicuvette rotors are disposed in spaced stacked relation in the compartment with a first air stream directed through the spaced rotors in the lower part of the stack, and a second air stream is flowed beneath the rotor stack through the compartment region and across the loading and analysis stations.

In accordance with still another aspect, an environmental control system that provides two air flow streams at different temperatures includes a refrigerant circuit that has first and second parallel circuit portions, means for flowing refrigerant through the two parallel circuit portions and flow control means for controlling the flow of refrigerant through each parallel circuit. First air flow circulation means flows a first air stream through a first recirculation loop in heat exchange relation to the first parallel circuit portion and control means responsive to the temperature of the first air stream controls the flow control means of the first parallel circuit portion to control thermal energy exchange between the first air stream and the first parallel circuit portion; and second air flow circulation means flows a second air stream through a second recirculation loop in heat exchange relation to the second parallel circuit portion and control means responsive to the temperature of the second air stream controls the flow control means of the second parallel circuit portion to control thermal energy exchange between the second air stream and the second parallel circuit portion.

In preferred embodiments, the first air stream is flowed through a first thermally insulated compartment in which analysis apparatus is housed to maintain that compartment at a controlled and stabilized temperature at which analyses are to be performed, and the second air stream is flowed through a second thermally insulated compartment in which sample and reagent materials are stored to maintain the sample and reagent materials stored therein at an appropriate storage temperature lower than the analysis temperature. The flow control means provides relatively slow changes in air stream temperature in linear manner over the controlled temperature range such that system stability is enhanced. Auxiliary heater means (in the form of an electric resistance heater in a particular embodiment) is in the first air circulation path and the control means responds to the first sensor (a thermistor) for also controlling the auxiliary heater means to provide more rapid adjustment of the temperature of the first air stream as required to maintain the desired analytical compartment temperature. A transfer mechanism that is arranged for movement between the two compartments and includes two pipettes and associated storage chambers that are maintained at the analysis temperature transfers metered quantities of sample and reagent from the first compartment for loading into the thermally equilibrated analytical cuvette at the loading station in the second compartment. As thermal equilibrium is established before sample and reagent materials are combined in the cuvette, improved controllability and verification of the analysis temperature and increased system accuracy and throughput results.

In a particular analyzer embodiment, the control means generates a desired temperature signal for each compartment (each desired temperature being operator selectable via a keyboard), each parallel circuit portion including evaporator means, evaporator pressure regulator means, a capillary tube section and capillary tube heater means. Each capillary tube and its heater are proportioned so that refrigerant flow is never blocked by that flow control and provide a smooth and substantially linear range of thermal exchange capacities—from about seventy to four hundred watts in the analytical compartment stream and from about fifty to two hundred watts in the storage compartment stream. Preferably, each capillary tube has an inner diameter of less than one millimeter and a length of less than one meter. Comparison means responds to each desired temperature signal and the corresponding actual air stream temperature and produces an error signal, and the power to each capillary tube heater is duty cycle modulated in response to the error signals. In that particular embodiment, the refrigerant circuit uses EPR valves with counterflow circuited evaporators to minimize temperature gradients, thus improving controllability and manufacturability. The motor for circulating the air flow in the analytical compartment is separately cooled, thus decreasing the heat load, reducing temperature gradients and increasing efficiency.

In preferred embodiments, the system has improved thermal efficiency as only the amount of thermal energy actually needed for maintaining temperature stability is added by the heater system. System accuracy is enhanced as both the cuvette and the reagent and sample materials have been equilibrated to the analysis temperature prior to cuvette loading, only the small quantities of sample and reagent material to be used in each reaction being heated (from storage temperature to analysis temperature) during the sequence of loading each cuvette. The system has small temperature gradients as heat exchange fluids are recirculated in thermally insulated recirculation paths that minimize heating requirements. The rotors, due to their long thermal time constants, maintain temperature stability even when the compartments are opened to add rotors, remove used rotors, add reagents and samples, etc. Air flow directers minimize heat loss when the compartments are opened. The system control permits selection of a particular analysis temperature in a self-calibrating system that is monitored by system software.

Other features and advantages of the invention will be seen as the following description of a particular embodiment progresses, in conjunction with the drawings, in which.

DESCRIPTION OF PARTICULAR EMBODIMENT

Figure 1:
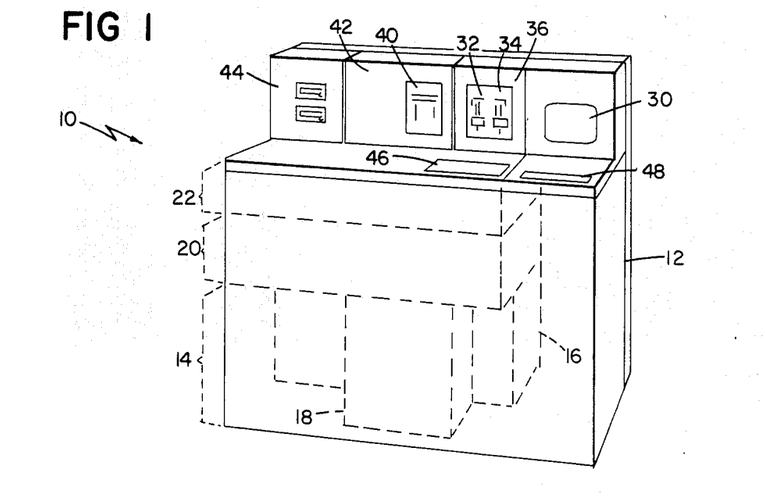
FIG. 1 is a perspective view of a centrifugal analyzer system in accordance with the invention.

The analysis system 10 shown in FIG. 1 is of the centrifugal analyzer type and includes a base housing 12 with a lower section 14 that houses heater-cooler apparatus 16 and electric circuit boards 18; an intermediate section 20 which houses drive motors and the like; and an upper section 22 which defines (see FIGS. 2 and 3) thermally isolated radiation source compartment 24, thermally isolated analysis compartment 26, and thermally isolated sample and reagent material storage compartment 28. Upstanding at the rear of base housing 12 is panel structure in which is located display 30; reagent metering pump apparatus 32 and sample metering pump apparatus 34 housed behind hinged access door 36; cuvette supply structure 38 housed behind window 40 in hinged access door 42; and magnetic tape reader apparatus 44. A sliding door access panel 46 in the top surface of base frame 12 provides access to storage compartment 28, and manual input control keyboard 48 is adjacent access door 46.

Figure 2:
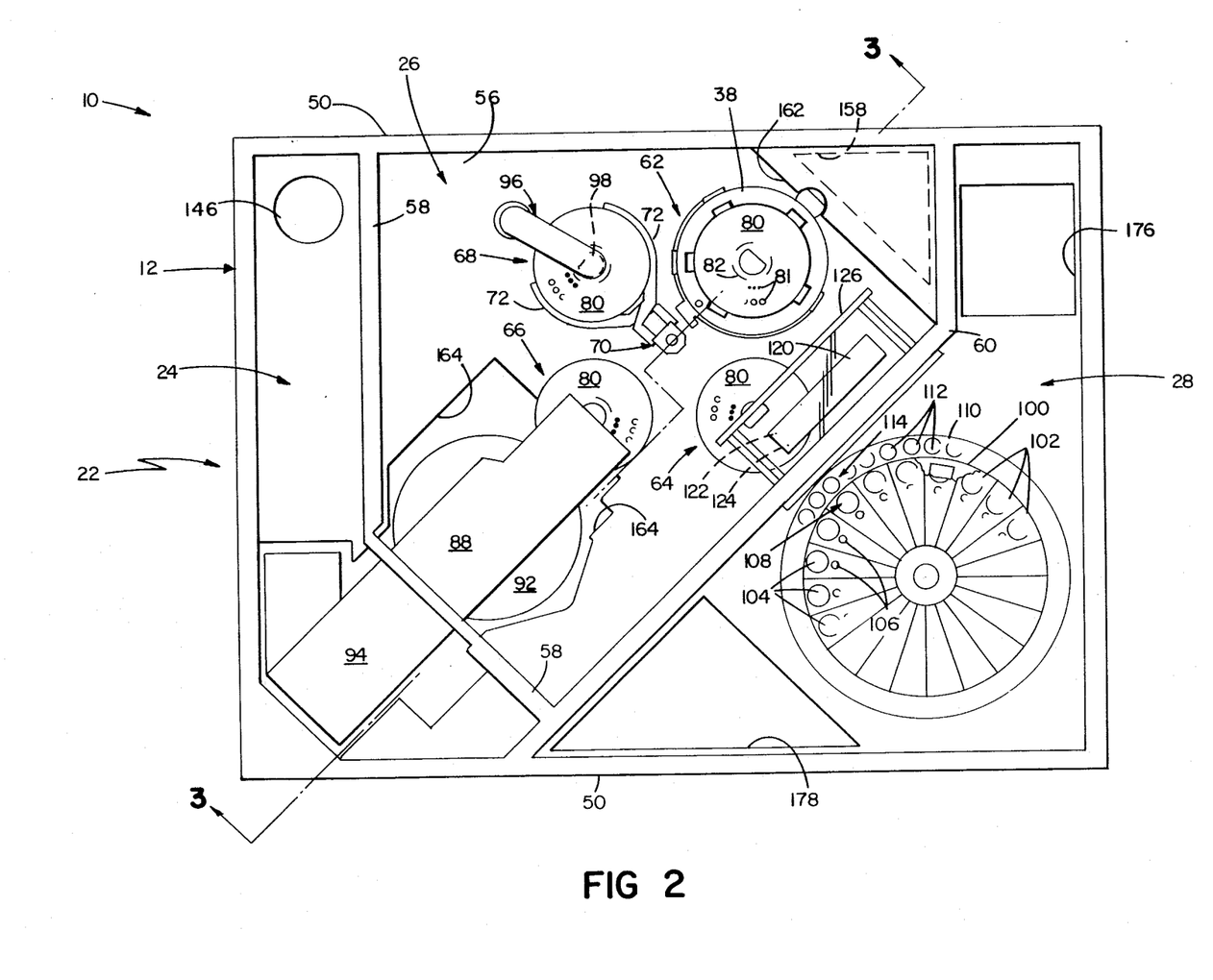
FIG. 2 is a top plan view of the source, analytical and storage compartments of the analyzer shown in FIG. 1.
Figure 3:
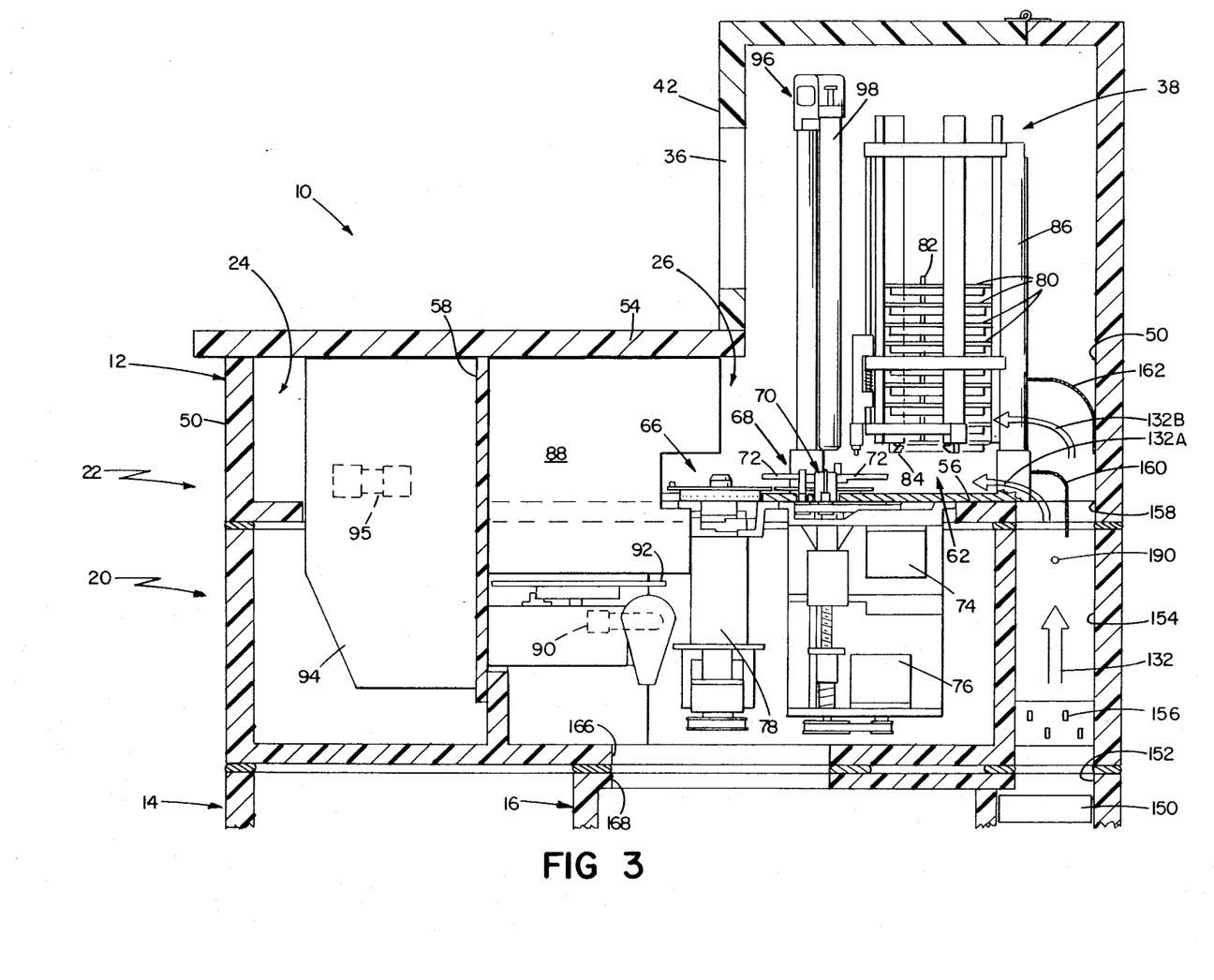
FIG. 3 is a sectional view taken along the line 3—3 of FIG. 2.

Further details of the source, analytical and storage compartments 24, 26 and 28 may be seen with reference to FIGS. 2 and 3. Section 22 is bounded by thermal isolation perimeter wall 50, by insulated cover wall 54, and by insulated floor 56 that supports mechanical handling mechanisms. Partition wall 58 separates radiation source compartment 24 from analytical compartment 26 and similar isolation wall 60 separates analysis compartment 26 from storage compartment 28. Disposed within analysis compartment 26 is supply station 62, loading station 64, analysis station 66, and used rotor station 68. Rotor transport mechanism 70 includes caliper arm structure 72 (which is adapted to grip a rotor 80 at its periphery) and drives 74, 76 (FIG. 3); while analysis station 66 includes drive 78 and a cuvette rotor indexing drive is located at loading station 64. Post structure 98 at used rotor station 68 receives rotors 80 after the contents have been analyzed for temporary storage and removal through access door 42. Further details of the source, analytical and storage compartments may be had with reference to co-pending U.S. patent application Ser. No. 706,073, filed concurrently herewith entitled CUVETTE HANDLING, the disclosure of which is incorporated herein by reference.

Analysis rotors 80 are of the type shown in the co-pending U.S. patent application Ser. No. 615,401 filed May 31, 1984 and entitled Cuvette Rotors For Centrifugal Analyzers, the disclosure of which is incorporated herein by reference, and are molded of acrylic polymeric material, each rotor 80 having a thermal time constant in the order of twenty minutes. Each rotor 80 defines a circumferential array of thirty-nine cuvettes, each with two loading ports 81, and has a diameter of about ten centimeters, and an overall body height of about one centimeter with three upstanding arcuate spacer ribs 82 that are about one-fourth centimeter high. Rotors 80 are stored in stacked relation in analysis compartment 26 in feeder tower structure 38, the rotor stack being supported by latch structure 84 at the base of the tower structure with the lower most rotor 80 being positioned for gripping by caliper arms 72 and individual removal from the stack for sequential transport to the loading, analysis and used rotor stations.

Adjacent analysis station 66 is optics compartment 88 with associated photosensor 90 and filter wheel 92. Spaced from compartment 88 by thermal isolation wall 58 is radiation source housing 94 which houses a radiation source such as Xenon lamp 95. A removable storage mechanism 96 at used rotor (discard) station 68 includes post 98 on which rotors 80 are inserted by transport mechanism 70 after their contents have been analyzed.

Disposed in operator compartment 28 is reagent table 100 (FIG. 2) on which is disposed an array of sector shape molded reagent containers 102, each of which has a transfer port 104 and a dry well port 106. An indexing mechanism (not shown) indexes reagent containers 102 past reagent station 108. A sample transport ring 110 surrounds reagent table 100 and carries sample cups 112. An indexing mechanism (not shown) indexes sample cups 112 sequentially past sample station 114.

Transport assembly 120 includes the heated storage chambers 118 (of about 100 and 250 microliter capacity) that are connected to pipette tubes 122 and 124 carried at its forward end, further details of which may be had with reference to co-pending application Ser. No. 706,070, filed concurrently herewith and entitled LIQUID HANDLING, and now U.S. Pat. No. 4,670,219, the disclosure of which is also incorporated herein by reference. Assembly 120 is moved between sample and reagent stations 114, 108, a wash station located in isolation wall 60, and loading station 64. Isolation chamber structure 126 houses pipette arm assembly 120 and has ports in its lower plate which provide access for the pipettes 122, 124 to the reagent and sample stations 108, 114 in the storage compartment 28 while the pipette arm assembly 120 is maintained substantially at the temperature of the analysis compartment 26.

Figure 4:
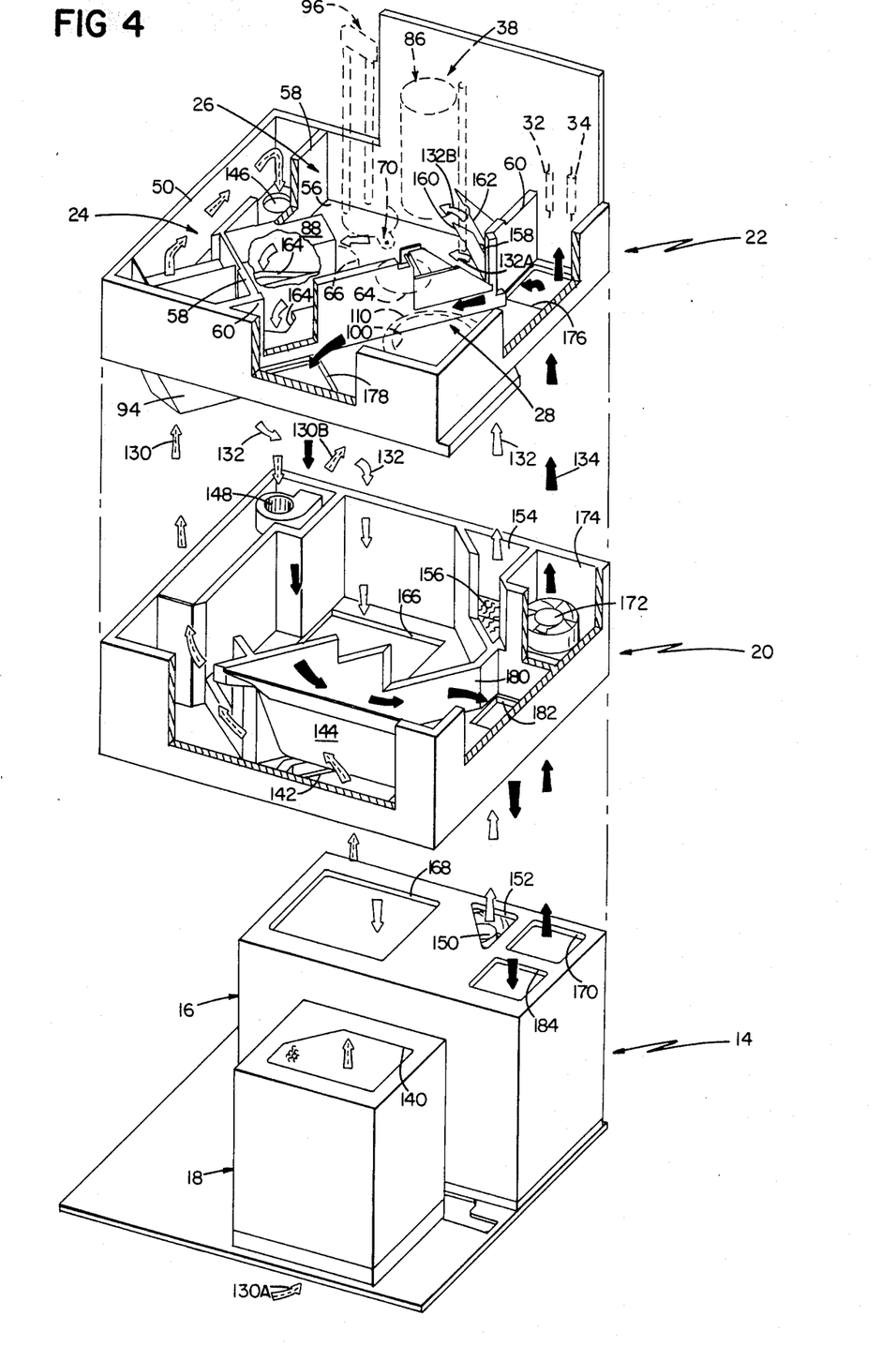
FIG. 4 is an exploded view diagram of sections of the analyzer system of FIG. 1 indicating air flow paths.

Three air flow paths are provided between the lower section 14 through the intermediate section 20 to the upper section 22. With reference to FIG. 4, the air flow for radiation source compartment 24 is indicated by shaded arrows 130; the air flow for analytical compartment 26 is indicated by outlined arrows 132, and the air flow for storage compartment 28 is indicated by solid arrows 134.

Air stream 130 is not recirculated and enters (arrow 130A) through the bottom of electronic circuit compartment 18 for upward flow through that compartment and exit through port 140 and entrance through port 142 into intermediate section 20. Inclined wall 144 directs air flow 130 laterally around radiation source housing 94 and upwardly through compartment 24 for discharge downwardly through port 146 as drawn by suction fan 148 for exhaust (arrow 130B) to the rear of intermediate section 20.

The air flow 132 through analytical compartment 26 is flowed by fan 150 in heater-cooler unit 16 (its motor 150M being separately housed) through port 152 upwardly via channel 154 in intermediate section 20 through heater structure 156 located in the base of that channel and past thermistor sensor 190 into channel extension 158 in upper section 22. Disposed in channel 158, as indicated in FIGS. 3 and 4, are lower and upper baffles 160, 162 that separate the air stream 132 into a lower stream 132A and an upper stream 132B. Upper baffle 162 directs portion 132B of the thermally conditioned air flow 132 in substantially horizontal flow through the lower part of the stack of rotors 80 (that are vertically spaced apart by arcuate spacer ribs 82) in feeder tower 86 to provide efficient thermal interchange between air flow 132 and those rotors as they approach the bottom of the stack so that each rotor at the bottom of the stack is thermally equilibrated; while lower baffle 160 directs the remaining portion 132A of the air flow 132 in a stream that sweeps beneath the rotor stack and across the bottom surface 56 of analytical compartment 26 at approximately the height of the rotors 80 at loading station 64 and analysis station 66 so that those stations are similarly thermally equilibrated. The thermal time constants of rotors 80 are such that the bottom rotor in the tower is thermally equilibrated (gradient of less than 0.3° C.) in about twenty minutes. Rotors 80 are resupplied through the top of tower 86 through access door 42, the rotors in the lower part of the stack remaining at equilibrated temperature while the door is open due to their long thermal time constants as well as the directed flow of air streams 132A and 132B beneath the top wall 54 of compartment 26. Stream 132 is exhausted from compartment 26 through ports 164 on either side of optics housing 88 and flows downwardly through intermediate section 20 and aligned apertures 166 and 168 for return to the heater-cooler unit 16 for thermal processing and recirculation through port 152.

Separate thermally processed air stream 134 emerges from heater-cooler unit 16 through port 170 as drawn by fan 172 for flow upwardly through isolation channel 174 past thermistor sensor 192 and entry into storage compartment 28 through port 176. In compartment 28, the air stream 134 flows upwardly around the metering pumps 32, 34 and transversely across reagent containers 102 and sample containers 112, and is exhausted through aperture 178 for downward flow through region 180 in intermediate section 20 and lower port 182 for return through port 184 in the upper wall of heater cooler unit 16 for thermal processing and recirculation through port 170.

Figure 5:
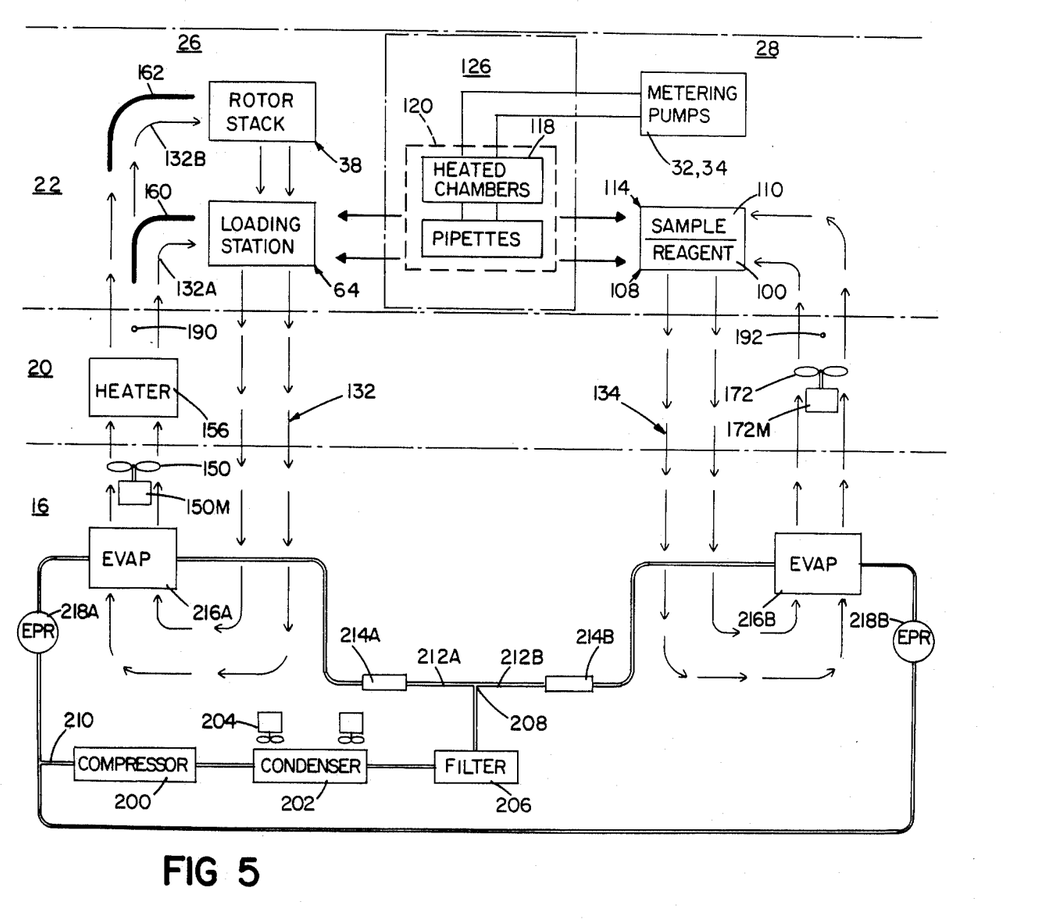
FIG. 5 is a block diagram of the heater-cooler module and air flow paths employed in the analyzer of FIG. 1.

A diagram of the heater-cooler module 16 and compartments 26 and 28 is shown in FIG. 5. Module 16 provides environmental control inputs for analytical compartment 26 and storage compartment 28. Air flow 132 through analysis compartment 28 (a flow rate of about 200 CFM and a total loop pressure drop of about two centimeters of water) is controlled to regulate the temperature in compartment 26 at a user selected temperature (for example 37° C.) within plus or minus 0.3° C. in response to monitoring thermistor 190 (located immediately below the baffles 160, 162 in channel 154 as indicated in FIG. 3) while the air flow 134 through storage compartment 28 (a flow rate of about 120 CFM and a total loop pressure drop of about 0.4 centimeters of water) is sensed by monitoring thermistor 192 to regulate the temperature in compartment 28 to the desired storage temperature (for example 15° C.) within plus or minus 2° C.

The basic refrigeration circuit shown diagrammatically in FIG. 5 includes a common circuit portion with one-third horsepower 4100 BTU per hour compressor 200 (Tecumseh Model 4440A) that circulates refrigerant (Freon 12) through finned heat exchange condensor 202 (with associated circulation fans 204) and filter-dryer 206 to junction 208. Two parallel circuits extend from junction 208 to the input 210 of compressor 200. Each parallel circuit includes capillary tube section 212 with heater 214, finned heat exchanger evaporator 216, and evaporator pressure regulator valve 218. Each capillary tube 212 and its heater 214 are proportional so that refrigerant flow is never blocked by the heater control, each tube 212 has an inner diameter of about 0.8 millimeter, tube 212A has a length of about thirty-six centimeters and tube 212B has a length of about eighty centimeters. Evaporators 216 are counterflow circuited to minimize temperature gradients and the evaporator pressure is regulated to provide decoupling of refrigerant flow between the two circuits and to minimize thermal gradients across the evaporators 216. EPR valve 218B is adjusted to maintain evaporator 216B completely flooded at a heat load of 200 watts (at 35° C. ambient air temperature) and a residual cooling level of about fifty watts with heater 214B fully on; and EPR valve 218B. Air stream 132 is flowed in the closed loop circulation path shown in FIGS. 4 and 5 upwardly by fan 150 from evaporator 216A through heater 156, past thermistor 190 for deflection by baffles 160, 162 across rotor stack 80 and through analytical compartment 26 for return to evaporator 216A; while air stream 134 is flowed upwardly by fan 172 past thermistor 192 through storage compartment 28 and return to evaporator 216B in a similar closed loop circulation path.

Figure 6:
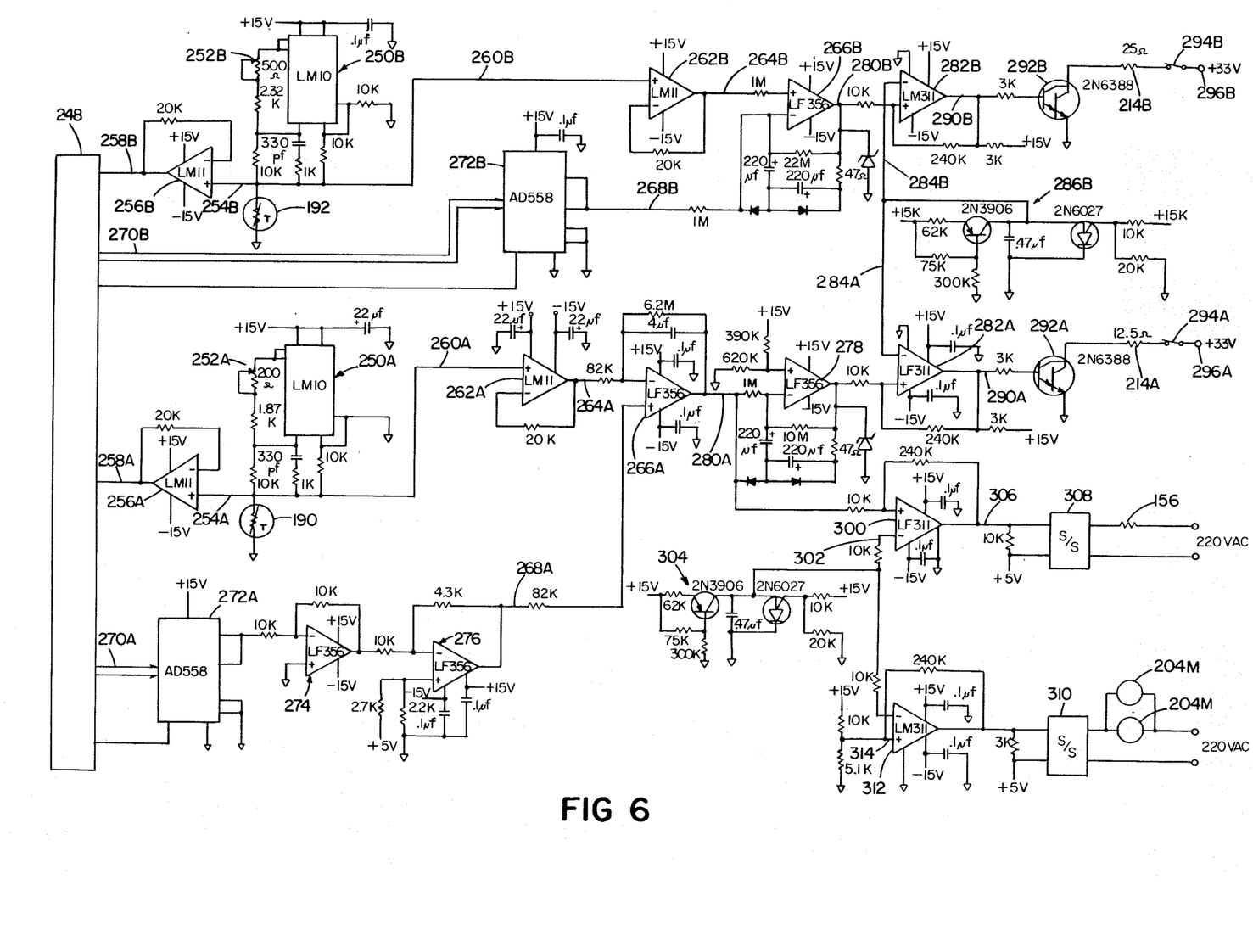
FIG. 6 is a schematic diagram of heater-cooler control circuitry.

Heater-cooler control circuitry is shown in FIG. 6. That circuitry includes sensing thermistors 190 and 192 (located immediately below analytical compartment 26 and storage compartment 28 respectively); capillary tube heaters 214A and 214B for refrigerant flow control; faster responding heater 156 for air stream 132; and fan motors 204M. The control circuitry responds to desired temperature signals supplied over cables 270A, 270B from central controller 248 and generates error signals as a function of actual sensed temperatures in the air flow circuits 132 and 134 to control heaters 156 and 214 and provides continual computer controlled monitoring and adjustment to maintain the temperatures of air flows 132, 134 within system tolerances.

Each thermistor sensor 190, 192 is fed from a current source 250 that includes current adjustment 252. A first temperature output is applied over line 254 through buffer amplifier 256 and line 258 as an analog signal to controller 248 and a second temperature output on line 260 is applied through buffer amplifier 262 to input line 264 of difference amplifier 266. Each difference amplifier 266 has a second analog input over line 268 from digital-to-analog converter 272. Digital-to-analog converter 272A in the channel for analysis compartment 26 receives a control signal over cable 270A from controller 248 specifying the desired analysis compartment temperature; and controller 248 generates a similar digital control signal over cable 270B for the control channel for storage compartment 28. Amplifier stages 274 and 276 in the analytical compartment monitoring channel map the analog voltage output of converter 272A to correspond to the characteristics of thermistor 190 over the 20° C.–40° C. range.

Each difference amplifier 266 responds to the desired temperature analog voltage signal from controller 248 on line 268 and the actual temperature signal on line 264 and generates an error signal on line 280 which, in the case of the analytical compartment channel is applied through filter amplifier 278 to comparator amplifier 282A and directly to amplifier 300, and in the case of the storage compartment channel is applied directly to comparator amplifier 282B. Differential amplifier 266A compares the desired temperature signal from controller 248 on line 268A with the actual air stream temperature signal on line 264A (applied to its minus input terminal) and generates a drive (temperature error) signal on line 280A which is applied to difference amplifier 278 which has an integrating feedback circuit (time constant of about thirty minutes) to provide an output which is applied through amplifier 282A to control capillary tube heater 214A in the refrigerant flow control to evaporator 216 to provide duty cycle temperature control of air stream 132. The voltage at the positive input of amplifier 278 establishes a steady state drive reference for heater 214A. The relatively slow response time of amplifier 278 provides improved operating efficiency, increases the overall dynamic range, and decreases temperature gradients in air stream 132 with resulting improved quality. The error signal on line 280A is also applied through amplifier 300 to control resistance heater 156. The much more rapid response of heater 156 provides supplemental adjustment of the temperature of air stream 132 so that its temperature is maintained with accuracy at the specified analytical compartment temperature.

Similarly, differential amplifier 266B in the storage compartment control channel responds to an actual temperature signal on line 264B that is applied to its plus input terminal (amplifier 266B having a long time constant feedback circuit and a control loop gain of $1+Z_F/Z_1$) and generates a heat request, the output signal on line 280B changing slowly and providing stable temperature control of the air flow stream 134 through the operator storage compartment 28. Thus, the temperature of compartment 28 temperature is duty cycle controlled by capillary tube heater 214B. The dual temperature control for compartment 26 includes the auxiliary or supplemental resistance heater 156 and the duty cycle modulated refrigerant flow control of capillary heater 214A. The control signals to heaters 156 and 214 are pulse width modulated. Each comparison amplifier 282 has a second input over line 284 from oscillator 286 that produces a saw tooth output signal (at a one kilohertz repetition rate) such that each amplifier 282 has an output on line 290 in the form of a pulse whose width varies as a function of the magnitude of the heat request signal on line 280. That output pulse is applied through Darlington pair 292 to provide pulse width modulation control of the associated capillary tube heater 214 that is connected in series with switch 294 to thirty-three volt source at terminal 296. The heat produced by heater 214 creates bubbles in the refrigerant which restricts flow in capillary line 212 (FIG. 5) and thus controls the refrigerant flow to its evaporator heat exchanger 216, each refrigerant flow control being proportioned (as indicated above) so that refrigerant flow is never totally blocked.

The analytical compartment temperature error signal is also applied to comparison amplifier 300 that has a second input on line 302 from saw tooth oscillator 304 that ramps from one volt to eleven volts at a four hertz repetition rate. The resulting series of output pulses of comparator 300 on line 306 switch solid state relay 308 at sixty (or fifty) hertz zero crossings to provide pulse width modulation control of six hundred watt air heater 156, the greater the error signal from differential amplifier 266A, the longer the duration of the output pulse on line 306. Solid state relay 308 switches at the zero crossing of the applied AC signal next following the leading edge of the pulse on line 306 to energize the six hundred watt air heater 156, that heater being deenergized at the AC signal zero crossing next following the end of each four hertz pulse.

The motors 204M of fans 204 are controlled by similar solid state relay 310 and comparison circuit 312 that has one input from oscillator 304 and a second input on line 314 from a preset voltage divider network, so that pulse width modulated power is applied to the fan motors 204M, causing the fans to run at about half speed and thus reducing audio noise.

In system operation, fan 150 circulates air stream 132 in a closed recirculation loop through evaporator 216A and heater 156 with a lower portion of air stream 132A being directed by baffle 160 for flow across the lower portion of analysis compartment 26 and an upper portion of air stream 132B being directed by baffle 162 for flow through the spaced rotors in feeder tower 38 to maintain the supply, loading and analysis stations at the analysis temperature that is operator specified via keyboard 48 and controller 248, the actual analysis compartment temperature being sensed by thermistor 190. Fan 172 circulates cooler (storage compartment temperature) air stream 134 in a second closed recirculation loop through evaporator 216B and storage compartment 28 for flow across the reagent and sample trays 100, 110. Rotors 80 are stored in feeder tower 38 and are fed sequentially (in thermally equilibrated condition) from supply station 62 and transported by mechanism 70 to loading station 64 where the rotor cuvettes (equilibrated to the analysis temperature) are loaded with sample and reagent materials which are drawn through pipettes 122, 124 into heated storage chambers 118 where their temperatures are rapidly increased towards the analysis temperature and then deposited into the cuvette in substantially thermally equilibrated condition. The loaded rotor may be transferred to the analysis station 66 as soon as loading is completed (without delay for thermal equilibration as in prior systems), and analyzed at the stable system analysis temperature by spinning the rotor to mix the sample and reagent materials and concurrently monitoring the several resulting reactions. After analysis, the rotor is transferred to used rotor station 68 for discard or for further loading if not all the cuvettes were utilized in the previous analyis sequence.

While a particular embodiment of the invention has been shown and described, various modifications will be apparent to those skilled in the art and therefore it is not intended that the invention be limited to the disclosed embodiment or to details thereof and departures may be made within the spirit and scope of the invention.

What is claimed is:

1. An analysis system of the fast centrifugal analyzer type, comprising
   a first storage area for storing sample materials at an appropriate storage temperature,
   a second area which is maintained at a controlled and stabilized higher temperature at which the analysis is to be performed, structure defining an analysis station and structure defining a supply station in said second area,
   means for storing a plurality of multicuvette rotors of long thermal time constant material adjacent said supply station structure for time intervals sufficient for those rotors to be equilibrated to the analysis temperature, said means for storing multicuvette rotors including feeder structure for disposing multicuvette rotors in spaced stacked relation,
   a thermal energy exchange system comprising a refrigerant circuit having a refrigerant circuit portion, means for flowing refrigerant through said circuit portion,
   flow control means for varying without blocking the flow of refrigerant through said circuit portion,
   flow circulation means for flowing an air stream through a recirculation loop in heat exchange relation to said circuit portion and through said second area,
   means for sensing the temperature of said air stream and operating said flow control means to control refrigerant flow in said circuit portion to maintain the temperature of said air stream substantially at said higher temperature,
   said flow circulation means flowing said air stream at said higher temperature through spaced multicuvette rotors in said stack in heat exchange relation thereto to thermally equilibrate multicuvette rotors to said analysis temperature,
   transport mechanism in said second area adapted to transport equilibrated multicuvette rotors sequentially from said supply station to said analysis station in said second storage area and then to a used rotor station, and
   transfer mechanism arranged for movement between said first and second storage areas for transferring a quantity of sample material from said first storage area for loading into an equilibrated rotor in said second storage area.

2. An analysis system of the fast centrifugal analyzer type comprising
   a thermally insulated compartment with a storage region, a plurality of multicuvette rotors of long thermal time constant material, means to support said multicuvette rotors in spaced stacked relation in said storage region,
   a loading region in said compartment,
   an analysis region in said compartment with measuring apparatus in sensing relation to said analysis region,
   transport mechanism for transporting rotors sequentially from said storage region to said loading region for loading with sample and reactant materials and then to said analysis region for chemical analysis,
   a thermal energy exchange system comprising a refrigerant circuit having a refrigerant circuit portion, means for flowing refrigerant through said refrigerant circuit portion,
   flow control means for varying without blocking the flow of refrigerant through said refrigerant circuit portion, flow circulation means for flowing a gas stream through a recirculation loop in heat exchange relation to said refrigerant circuit portion and through said compartment, means for sensing the temperature of said gas stream and operating said flow control means to control refrigerant flow in said refrigerant circuit portion to maintain the temperature of said gas stream at a controlled stabilized analysis temperature, said flow circulation means circulating gas at said controlled stabilized analysis temperature through the storage region to provide efficient thermal interchange between stored rotors to stabilize the temperature of those rotors at the analysis temperature prior to transfer of a rotor from said storage region to said loading region for loading with sample and reactant materials, said flow circulation means including means for directing a first gas stream through spaced rotors in said rotor support means, and a second gas stream beneath said rotor support means through said compartment and across said loading and analysis regions.

3. A fast centrifugal analyzer system comprising a first thermally insulated compartment, means for storing sample and reagent materials in said first compartment, a second thermally insulated compartment that is thermally insulated from said first compartment, a supply station and a loading station in said second compartment, means for maintaining said first compartment at an appropriate storage temperature including means for circulating a first stream of gas at said storage temperature through said first compartment, means for maintaining said second compartment at a controlled and stabilized analysis temperature that is higher than said storage temperature including means for circulating a second stream of gas at said analysis temperature through said second compartment, a plurality of centrifugal analyzer rotors, each said centrifugal analyzer rotors having a plurality of cuvettes, means for storing said plurality of centrifugal analyzer rotors of long thermal time constant material in said second compartment at said supply station including means for directing said second stream of gas over said rotors at said supply station to equilibrate said stored analysis rotors to said analysis temperature, a thermal energy exchange system comprising a refrigerant circuit having first and second parallel circuit portions, means for flowing refrigerant through said two parallel circuit portions, and flow control means for varying without blocking the flow of refrigerant through each said parallel circuit portion, said means for maintaining said first compartment at an appropriate storage temperature including said first stream circulation means for flowing said first stream through a first closed loop in heat exchange relation to said first parallel circuit portion and through said first compartment and means for sensing the temperature of said first stream and operating said flow control means to control refrigerant flow in said first parallel circuit portion to maintain the temperature of said first stream substantially at said storage temperature, said means for maintaining said second compartment at said analysis temperature including said second stream circulation means for flowing said second stream through a second closed recirculation loop in heat exchange relation to said second parallel circuit portion and through said second compartment, and means for sensing the temperature of said second stream and operating said flow control means to control refrigerant flow in said second parallel circuit portion to maintain the temperature of said second stream substantially at said analysis temperature, transport means in said second compartment for transporting a thermally equilibrated rotor from said supply station to said loading station, transfer means including heater means for transferring predetermined quantities of sample and reagent materials from said first compartment for loading into a cuvette of an equilibrated rotor at said loading station, and means in said second compartment for analyzing the mixtures of sample and reagent materials in the cuvettes of a rotor.

4. The system of claim 3 and further including auxiliary heater means in said second air stream circulation loop and control means responsive to said means for sensing the air temperature of said second air stream for controlling said auxiliary heater means to provide supplement adjustment of the temperature of said second air stream.

5. The system of claim 4 wherein each said parallel circuit portion includes a capillary tube section and said flow control means includes a heater for each said capillary tube section.

6. The system of claim 3 and further including means for generating a desired analysis temperature signal, means for generating an actual temperature signal indicative of the actual temperature of said analysis compartment, comparison means for comparing said desired and actual temperature signals and producing an error signal responsive to a difference between said actual and desired temperature signals, and means responsive to said error signal for controlling said second compartment temperature maintaining means.

7. The system of claim 6 wherein said comparison means includes a difference amplifier which has an integrating feedback circuit and further including means responsive to said error signal for pulse width modulating a control signal applied to said second compartment temperature maintaining means.

8. A centrifugal analyzer system comprising a first thermally insulated compartment, means for storing sample and reagent materials in said first compartment, a second thermally insulated compartment that is thermally insulated from said first compartment, a supply station and a loading station in said second compartment, means for maintaining said first compartment at an appropriate storage temperature including means for circulating a first stream of gas at said storage temperature through said first compartment, means for maintaining said second compartment at a controlled and stabilized analysis temperature that is higher than said storage temperature including means for circulating a second stream of gas at said analysis temperature through said second compartment, a plurality of centrifugal analyzer rotors of long thermal time constant material, each said rotor having a plurality of cuvettes, means for storing said plurality of centrifugal analyzer rotors in said second compartment at said supply station including means for directing said second stream of gas over rotors at said supply station to equilibrate each rotor to said analysis temperature, a thermal energy exchange system comprising a refrigerant circuit having first and second parallel circuit portions, each said parallel circuit portion including a capillary tube section that has a length of less than one meter and an inner diameter of less than one millimeter, means for flowing refrigerant through said two parallel circuit portions, and flow control means for controlling the flow of refrigerant through each said parallel circuit portion, said flow control means including a heater for each said capillary tube section, each said capillary section tube and its heater being proportioned so that refrigerant flow is never blocked by said flow control means, said means for maintaining said first compartment at an appropriate storage temperature including said first stream circulation means for flowing said first stream through a first closed loop in heat exchange relation to said first parallel circuit portion and through said first compartment and means for sensing the temperature of said first stream and operating said flow control means to control refrigerant flow in said first parallel circuit portion to maintain the temperature of said first stream substantially at said storage temperature, said means for maintaining said second compartment at said analysis temperature including said second stream circulation means for flowing said second stream through a second closed recirculation loop in heat exchange relation to said second parallel circuit portion and through said second compartment, and means for sensing the temperature of said second stream and operating said flow control means to control refrigerant flow in said second parallel circuit portion to maintain the temperature of said second stream substantially at said analysis temperature, transport means in said second compartment for transporting a thermally equilibrated rotor from said supply station to said loading station, transfer means including heater means for transferring predetermined quanitites of sample and reagent materials from said first compartment for loading into a cuvette of an equilibrated rotor at said loading station, and means in said second compartment for analyzing the mixtures of sample and reagent materials in the cuvettes of a rotor.

9. The system of claim 8 wherein said refrigerant circuit includes a compressor, each said parallel circuit portion includes evaporator means, evaporator pressure regulator means, and a capillary tube section, and said flow control means includes a heater for each said capillary tube section.

10. The system of claim 9 and further including means for generating a desired first compartment temperature signal, means for generating an actual temperature signal indicative of the actual temperature of said first compartment, first comparison means for comparing said desired and actual first compartment temperature signals and producing a first error signal responsive to a difference between said actual and desired temperature signals, and means responsive to said first error signal for controlling the capillary tube heater of said first compartment temperature maintaining means, means for generating a desired analysis compartment temperature signal, means for generating an actual temperature signal indicative of the actual temperature of said analysis compartment, second comparison means for comparing said desired and actual analysis compartment temperature signals and producing a second error signal responsive to a difference between said actual and desired temperature signals, and means responsive to said second error signal for controlling the capillary tube heater of said analysis compartment temperature maintaining means and said auxiliary heater means.

11. The system of claim 10 and further including means responsive to each said error signal for pulse width modulating control signals applied to said capillary tube heaters.

12. A centrifugal analyzer system comprising a first thermally insulated compartment, means for storing sample and reagent materials in said first compartment, a second thermally insulated compartment adjacent to and thermally insulated from said first compartment, said first and second compartments including a thermally insulated common wall, a passage in said common wall, a supply station and a loading station in said second compartment, means for maintaining said first compartment at an appropriate storage temperature including means for circulating a first stream of gas at said storage temperature through said first compartment, means for maintaining said second compartment at a controlled and stabilized analysis temperature that is higher than said storage temperature including means for circulating a second stream of gas at said analysis temperature through said second compartment, means for storing a plurality of centrifugal analyzer rotors of long thermal time constant material in said second compartment at said supply station including means for directing said second stream of gas over rotors at said supply station to equilibrate each rotor to said analysis temperature, transport means in said second compartment for transporting a thermally equilibrated rotor from said supply station to said loading station, transfer means for transferring predetermined quantities of sample and reagent materials from said first compartment for loading into a cuvette of an equilibrated rotor at said loading station, said transfer mechanism including a pair of liquid handling probes, a probe transport carriage on which said liquid handling probes are mounted, a drive for moving said transport carriage through said passage in said common wall between said first and second compartments, said transport carriage including a reagent storage chamber connected to one of said liquid handling probes and a sample storage chamber connected to the other of said liquid handling probes, each said storage chamber having a capacity of less than one milliliter, and heater means including thermal energy supplying means in heat exchange relation with said storage chambers, and means in said second compartment for analyzing the mixtures of sample and reagent materials in the cuvettes of a rotor.

13. The system of claim 12 wherein said analyzing means in said second compartment includes an optics module and further including means for cooling said optics module external to and independently of said first and second compartments.

14. The system of claim 13 and further including a thermal energy exchange system comprising a refrigerant circuit having first and second parallel circuit portions, means for flowing refrigerant through said two parallel circuit portions, and flow control means for controlling the flow of refrigerant through each said parallel circuit portion, said means for maintaining said first compartment at an appropriate storage temperature includes said first stream circulation means for flowing a first air stream through a first closed loop in heat exchange relation to said first parallel circuit portion and through said first compartment and means for sensing temperature of said first air stream and operating said flow control means to control refrigerant flow in said first parallel circuit portion to maintain the temperature of said first air stream substantially at said storage temperature, said means for maintaining said second compartment at said analysis temperature includes said second stream circulation means for flowing a second air stream through a second closed recirculation loop in heat exchange relation to said second parallel circuit portion and through said second compartment, and means for sensing the air temperature of said second air stream and operating said flow control means to control refrigerant flow in said second parallel circuit portion to maintain the temperature of said second air stream substantially at said analysis temperature, and further including means for directing said second air stream over said rotors at said supply station to equilibrate each said rotor to said analysis temperature prior to transfer of said rotor from said supply station to said loading station.

15. The system of claim 14 and further including means for generating a desired temperature signal for each said air stream, comparison means responsive to each said desired temperature signal and the actual temperature signal of its corresponding air stream for producing an error signal, means responsive to said error signal for pulse width modulating said refrigerant flow control means, auxiliary heater means in said first air stream circulation loop and means responsive to said error signal for controlling said auxiliary heater means to provide supplemental adjustment of the temperature of said first air stream, the response time of said auxiliary heater control means being at least ten times faster than the response time of said flow control means.

16. A system of the centrifugal analyzer type including a thermally insulated compartment a plurality of multicuvette rotors of long thermal time constant material, a storage region in said compartment for said plurality of multicuvette rotors, means to support said multicuvette rotors in spaced stacked relation in said compartment, a loading region in said compartment, an analysis region in said compartment with measuring apparatus in sensing relation to a multicuvette rotor at said analysis station, and transport mechanism for transporting multicuvette rotors sequentially from said storage station to said loading station for loading with sample and reactant materials and then to said analysis station for chemical analysis in said compartment, flow circulation means for flowing an air stream through a recirculation loop that includes said compartment, said air stream circulating means including main thermal energy exchange means in said recirculation loop, said main thermal energy exchange means including a refrigerant circuit having means for flowing refrigerant through the circuit that includes a compressor, evaporator means, evaporator pressure regulator means, and flow control means for controlling the flow of refrigerant through said circuit that includes capillary tube section and a heater for said capillary tube section, said capillary tube having a length of less than one meter and an inner diameter of less than one millimeter, and said capillary tube and its heater being proportioned so that refrigerant flow is never blocked by said flow control means, auxiliary heater means in said recirculation loop, means for sensing the air temperature of said air stream, means for generating a desired temperature signal for said air stream, comparison means responsive to said desired temperature signal and the actual temperature signal of said air stream for producing an error signal, and means responsive to said error signal for controlling said main thermal energy exchange means to establish an air stream temperature and for controlling said auxiliary heater means to provide supplemental adjustment of the temperature of said air stream to provide a controlled stabilized air stream temperature, the response time of said auxiliary heater control being at least ten times faster than the response time of said main thermal energy exchange control, and means in said compartment for directing a first air stream through the spaced rotors in the lower part of said stack, and a second air stream beneath said rotor stack through said compartment and across said loading and analysis stations, said air stream at said controlled stabilized temperature being circulated through said compartment to provide efficient thermal interchange between said stored multicuvette rotors to stabilize the temperature of those stored rotors at the temperature of said air stream prior to transfer of said rotors from said storage region to said loading region for loading with sample and reactant materials.

17. The system of claim 16 and further including a second thermally insulated compartment, means for storing sample and reagent materials in said second compartment, means for maintaining said second compartment at an appropriate storage temperature that is lower than said analysis temperature, and transfer mechanism including heater means for transferring predetermined quantities of sample and reagent materials from said second compartment for loading into a cuvette of an equilibrated rotor at said loading station, said transfer mechanism including a pair of liquid handling probes, a probe transport carriage on which said liquid handling probes are mounted, a drive for moving said transport carriage between said first and second compartments, said transport carriage including a reagent storage chamber connected to one of said liquid handling probes and a sample storage chamber connected to the other of said liquid handling probes, each said storage chamber having a capacity of less than one milliliter, and said heater means includes thermal energy supplying means in heat exchange relation with said storage chambers.

18. The system of claim 17 wherein said comparison means includes a difference amplifier which has an integrating feedback circuit and further including means responsive to said error signal for pulse width modulating a control signal applied to said second compartment temperature maintaining means.

* * * * *

UNITED STATES PATENT AND TRADEMARK OFFICE
CERTIFICATE OF CORRECTION

PATENT NO. : 4,708,886

DATED : November 24, 1987

INVENTOR(S) : Larry A. Nelson

It is certified that error appears in the above-identified patent and that said Letters Patent are hereby corrected as shown below:

Column 1, line 2, before "apparatus" --to-- should be inserted.

Claim 1, column 10, line 8, "plurality" is misspelled.

Claim 16, line 29, After "includes" --a-- should be inserted.

Under the References Cited section, the following references listed the Information Disclosure Statement should be included:

| | |
|---|---|
| 3,811,842 | Diebler |
| 3,916,152 | Hinman |
| 3,981,437 | Hemfort |
| Re 29,880 | Duff |
| 4,298,571 | DeFulvio |
| 4,311,667 | Gocho |
| 4,313,735 | Yamashita |
| 4,341,736 | Drbal |
| 4,344,768 | Parker |
| 4,360,360 | Chiknas |
| 4,373,812 | Stein |

UNITED STATES PATENT AND TRADEMARK OFFICE
CERTIFICATE OF CORRECTION

PATENT NO. : 4,708,886                      Page 2 of 2

DATED       : November 24, 1987

INVENTOR(S) : Larry A. Nelson

It is certified that error appears in the above-identified patent and that said Letters Patent is hereby corrected as shown below:

Hitachi 705 (1981) Fully Automated Chemistry Analyzer, Boehringer Mannheim Diagnostics.

Signed and Sealed this

Sixth Day of September, 1988

*Attest:*

DONALD J. QUIGG

*Attesting Officer*            *Commissioner of Patents and Trademarks*